United States Patent [19]

Berger et al.

[11] Patent Number: 4,994,378

[45] Date of Patent: Feb. 19, 1991

[54] METHOD FOR REDUCING BLOOD CARBON DIOXIDE BACKGROUND IN BACTERIAL MEDIA BY THE ADDITION OF MICELLES OF SAPONIN AND A PHOSPHOLIPID

[75] Inventors: Dolores M. Berger, Baltimore; Paul E. Goldenbaum, Towson; Gregory Tice, Lutherville, all of Md.

[73] Assignee: Becton, Dickinson and Company, Franklin Lakes, N.J.

[21] Appl. No.: 404,475

[22] Filed: Sep. 8, 1989

[51] Int. Cl.$^5$ .............................................. C12Q 1/02
[52] U.S. Cl. ...................................... 435/29; 435/31; 435/34
[58] Field of Search .............................. 435/29, 34, 31

[56] References Cited

U.S. PATENT DOCUMENTS

| | | |
|---|---|---|
| 3,676,679 | 7/1972 | Waters . |
| 3,854,041 | 12/1974 | Waters . |
| 3,858,045 | 12/1974 | Waters . |
| 3,935,073 | 1/1976 | Waters . |
| 4,073,691 | 2/1978 | Ahnell et al. .................. 435/34 |

OTHER PUBLICATIONS

Interaction of Saponin and Digitonin with Black Lipid Membranes and Lipid Monolayers, Gogelein et al., *Biochimica et Biophysica Acta*, 773, 32–38 (1984).

Simplified Lysed-Blood Culture Techniques, Zierdt, *Journal of Clinical Microbiology*, 23, 452–455, (1986).

The Phospholipid-Cholesterol Interaction Kinetics of Water Permeability in Liposomes, Bittmann et al., *Biochemistry*, 11, 4831–4839, (1972).

Fusion of Dipalmitoylphosphatidylcholine Vesicles, Schullery et al., *Biochemistry*, 19, 3919–3923 (1980).

*Primary Examiner*—Sam Rosen
*Attorney, Agent, or Firm*—Robert M. Hallenbeck

[57] ABSTRACT

A non-ionic lytic agent, preferably saponin for reducing the background carbon dioxide produced by blood cell metabolism is used in the testing of cultures for the presence of microorganisms. The hemolytic agent saponin is combined with a phospholipid, preferably L-α-Lecithin (phosphatidylcholine), to form mixed micelles which protect saponin from the effects of heat sterilization and high blood cholesterol levels, thus maintaining the lytic activity of saponin. The phospholipid/saponin mixed micelles are added to non-radiometric culture media vials such as Bactec® NR6A, NR7A and NR8A. The media vials are used in the Bactec® NR-660 and NR-730 instruments. However, the present invention may also be used in radiometric media such as Bactec® culture vials 6, 7 and 8 for reducing background carbon dioxide levels detected in $C^{14}$ radiometric instruments such as the Bactec®-460, or in other instruments designed to detect bacteria in the presence of mammalian cells by monitoring the increase in $CO_2$ produced by the metabolizing bacteria.

23 Claims, 8 Drawing Sheets

FIGURE 1.

FIGURE 3.
DONOR I: SERUM TOTAL CHOLESTEROL 164mg/dL

FIGURE 4.
DONOR II: SERUM TOTAL CHOLESTEROL 179mg/dL

FIGURE 5.
DONOR III: SERUM TOTAL CHOLESTEROL 239mg/dL

FIGURE 6.

FIGURE 7.
DONOR VI: SERUM TOTAL CHOLESTEROL 167mg/dL

FIGURE 8.
DONOR VII: SERUM TOTAL CHOLESTEROL 215mg/dL

METHOD FOR REDUCING BLOOD CARBON DIOXIDE BACKGROUND IN BACTERIAL MEDIA BY THE ADDITION OF MICELLES OF SAPONIN AND A PHOSPHOLIPID

BACKGROUND OF THE INVENTION

1. Field of the Invention

This invention relates to a method for reducing the carbon dioxide background due to blood metabolism in a bacterial medium by the addition of a mixture of saponin and a phospholipid to maintain the lytic activity of saponin over a broad concentration range of blood cholesterol levels in the sample and preserve the lytic activity of saponin containing media after heat sterilization.

2. Background of the Related Art

Automated diagnostic instruments such as the Bactec ® 460, the Bactec ® NR-660 and NR-730 manufactured by Becton Dickinson Diagnostic Instrument Systems, 383 Hillen Road, Towson, Md., are used in clinical microbiology laboratories to detect increases in carbon dioxide levels caused by microorganisms metabolizing a carbon source in a culture vial which holds the sample and medium. One primary use of the instrument is the detection of suspected septicemia caused by the presence of microorganisms in the blood of a patient. The presence of living blood cells in the sample being tested complicates these measurements by evolving additional carbon dioxide into the head space of a container for the sample. These clinical instruments do not distinguish between the carbon dioxide produced by the metabolism of a microorganism and the carbon dioxide produced by blood cell metabolism.

Automated instruments for the testing of blood cultures are described in U.S. Pat. Nos. 3,676,679 and 3,935,073 to Waters. The process involves the use of a growth medium containing a $C^{14}$ carbon source which can be metabolized to produce gaseous $C^{14}O_2$. A sample of blood to be tested is added to the growth medium and after a suitable period of incubation a portion of the gaseous atmospheres is tested for the presence of radioactive $C^{14}$. The Waters patents do not address the reduction of background carbon dioxide formed by blood cell metabolism.

An improved process to those described in the above Waters patents is set forth in U.S. Pat. No. 3,854,041 to Waters, et al. The improvement requires the addition to the growth medium of a material such as sucrose, raffinose or glycylglycine in order to reduce the incidence of high background readings due to sterile blood.

U.S. Pat. No. 3,858,045 to Waters described the use of physical, osmotic or chemical lysis of blood cells to reduce the background $CO_2$ readings due to blood metabolism. The '045 patent discloses non-ionic detergents such as polyoxyethylene, sorbitan and saponin as effective chemical lytic agents for use in radiometric culture media vials which effectively reduce the background carbon dioxide reading due to blood cell metabolism.

All of the above-described Waters and Waters et al. patents are directed towards the use and analyses of cultures in automated Bactec ® radiometric $C^{14}O_2$ detection instruments such as the Bactec ® 460.

The method and apparatus utilized in the Bactec ® NR-660 and NR-730, do not require the utilization of radioactive $C^{14}$ in the culture medium. Rather, the growth of microorganisms in the cultures is detected by sampling the headspace gas present over the growth medium and measuring the carbon dioxide concentration in that gas by infrared analysis. This method and apparatus is described in U.S. patent application Ser. No. 597,633 (filed on Apr. 6, 1984). A modification of the method and apparatus described in Ser. No. 597,633 in which a direct non-invasive method for the analysis of the gaseous atmosphere container over the growth medium uses infrared absorption through the side walls of the container for the media is described in pending U.S. patent application Ser. No. 686,327 (filed Dec. 24, 1984). The disclosure of both of these patent applications are incorporated by reference in this application.

The inventors, herein, have successfully used the lytic agents described by U.S. Pat. No. 3,858,045 to Waters in the non-radiometric Bactec ® NR-660 and NR-730 instruments. Saponin, a non-ionic detergent plant extract, was especially effective in reducing blood carbon dioxide backgrounds while remaining non-toxic to most organisms. It was found, however, that the lytic activity of saponin is decreased significantly by heat sterilization, losing about ½ of its lytic activity when saponin is present in dilute concentrations in media, i.e. less than 2 mg/ml.

The inventors, herein, have also discovered that the presence of cholesterol in blood serum significantly reduced the lytic activity of saponin. This discovery is consistent with the reported findings of Gogelein, et al., in *Biochimica et Biophysica Acta*, 773, 32–38 (1984), that saponin binds preferentially to cholesterol.

Accordingly, it is in object of this invention to provide a method for reducing the background carbon dioxide level in blood cultures due to the presence of mammalian cells, without inhibiting the metabolic activity of microorganisms present in the culture.

Another object of this invention is to provide a culture medium for reducing the background carbon dioxide level in blood cultures due to the presence of mammalian cells, without inhibiting the metabolic activity of microorganisms utilizing a non-ionic detergent which does not lose its lytic activity after the medium has been autoclaved.

A further object of this invention is to provide a culture medium for reducing the background carbon dioxide level in blood cultures due to the presence of mammalian cells without inhibiting the metabolic activity of microorganisms present in the culture, utilizing a non-ionic detergent which will not lose its lytic activity due to high cholesterol levels in the blood being sampled.

SUMMARY OF THE INVENTION

These and other objects are achieved by the present invention which provides a non-ionic detergent lytic agent, preferably saponin, for reducing the background carbon dioxide produced by blood cell metabolism. The lytic agent, such as saponin is combined with a phospholipid, preferably L-α-Lecithin (phosphatidylcholine), to form mixed micelles which protect saponin containing medium from the effects of heat sterilization and high blood cholesterol levels, thus maintaining its lytic activity. The preferred method of the present invention involves incorporating the saponin into micelles of the phospholipid. The saponin-phospholipid mixed micelles are added to vials containing non-radiometric culture medium such as Bactec ® NR6A, NR7A and NR8A. These media are used in the Bactec ® NR-660 and NR-730 instruments. However, the present invention may also be used in radiometric media such as Bactec ® culture vials 6, 7 and 8 for reducing background carbon dioxide levels detected as $C^{14}$ in radiometric detection instruments such as the Bactec ® -460, or in other instruments designed to detect bacteria in the presence of mammalian cells by monitoring the increase in $CO_2$ produced by the metabolizing bacteria.

For a better understanding of the present invention, reference is made to the following description and examples, taken in conjunction with accompanying table and figures, the scope of which is pointed out in the appended claims.

BRIEF DESCRIPTION OF THE DRAWINGS

FIG. 4 is a graph illustrating the reduction of blood $CO_2$ background readings of blood from a low cholesterol donor (Donor II-179 mg/dL) after adding PC and saponin to media either separately (first method), or as a sonicated mixed-micelle suspension (second method). Each sample contained 5 ml blood from Donor II. The control, shown as the solid line, contained 30 ml modified Bactec ® NR6A medium. Another control contained 30 ml modified Bactec ® NR6A medium to which soy PC liposomes were added ("△"). One sample contained modified Bactec ® NR6A medium to which 6 mg saponin was added ("□"). A second sample contained modified Bactec ® NR6A medium to which 6 mg saponin and 5 mg of soy PC liposomes were added ("O"). The third sample contained modified Bactec ® NR6A medium to which 0.5 ml of a sonicated mixed-micelle solution of soy PC (100 mg) and saponin (120 mg) was added ("*"), as described in Example 3.

FIG. 6 is a graph illustrating the blood $CO_2$ background readings for various types of modified Bactec ® NR6A media, which contain blood from a high cholesterol Donor IV and from a low cholesterol Donor V. The controls, one containing modified Bactec ® NR6A medium and 5 ml blood from Donor IV ("●") the other containing modified Bactec ® NR6A medium and 5 ml blood from Donor V ("■"); the saponin only test samples, one containing the modified medium with 6 mg saponin and 5 ml blood from Donor IV ("□"), another containing the modified medium with 6 mg saponin and 5 ml blood from Donor V ("*"); the preferred medium samples, one containing the modified medium with PC and saponin mixed-micelles and 5 ml blood from Donor IV ("△"), and the other containing the modified medium with PC and saponin mixed-micelles and 5 ml blood from Donor V ("O"), as described in Example 4.

DETAILED DESCRIPTION OF THE INVENTION

In cases of suspected septicemia, i.e. microorganism invasion of the blood, a blood sample is withdrawn from the patient with a syringe utilizing aseptic techniques. The blood sample, approximately 1-10 ml is injected into a vial containing a growth medium suitable for the support and growth of suspected microorganisms contained in the blood sample. The growth medium contains compounds which can be metabolized by the microorganism to form carbon dioxide. The pH of the growth medium is adjusted to near neutrality since growth of the microorganism generally reduces the pH of the medium. Some of the carbon dioxide produced as a metabolic by-product of the growth metabolism of the microorganism in the medium is released into the "head space" of the vial over the growth medium.

Suitable commercially available non-radiometric culture vials containing growth media include the Bactec ® NR6A culture vials containing enriched soybean-casein digest broth with $CO_2$ for detection of growth in aerobic cultures, the Bactec ® NR7A culture vials containing prereduced enriched soybean-casein digest broth with $CO_2$ for nonradiometric detection of anaerobic growth of cultures, and the Bactec ® NR8A culture vials containing hypertonic enriched soybean-casein digest broth with $CO_2$ for aerobic cultures. These culture vials are utilized in the Bactec ® NR-660 and NR-730 instruments as described in the Background of the Invention. In addition, culture vials utilizing $C^{14}$ labelled media are also commercially available, these include the Bactec ® 6B, 7D and 8A culture vials. Bactec ® is a trademark of Becton Dickinson Diagnostic Instruments Systems, 383 Hillen Road, Towson, Md. 21204. These commercially available culture vials typically contain 30 milliliters of growth medium in a vial having a total capacity of about 60 milliliters. A more detailed description of the Bactec ® non-radiometric culture vials NR6, NR7 and NR8 is described in Becton Dickinson Brochure MA-0034, PP-044A dated November, 1987. The radiometric culture vials are described in more detail in Becton Dickinson Brochure PP-014G dated October 1987.

Following inoculation, the growth medium is subjected to conditions suitable to promote growth of a suspected microorganism present in the blood sample. After sufficient incubation time, usually in the range of 4 to 24 hours, the vial is placed in an instrument designed to monitor increases in carbon dioxide concentration in the head space of the vial over the growth media, for example, the Bactec ® NR-660 and 730 instruments are suitable for use with nonradiometric growth media culture vials, and the Bactec ® 460 instrument is suitable for use with radiometric growth media culture vials. The Bactec ® 460 instrument monitors the increases in carbon dioxide concentration by counting radioactive $C^{14}$ in an ionization chamber, and the Bactec ® NR-660 and the NR-730 instruments monitor the increases in carbon dioxide concentration by the use of infrared analysis of the head space gas.

A clinical sample being tested should preferably not cause an increase in the level of carbon dioxide because of the intrinsic properties of the sample, such as the metabolism of living mammalian cells. However, a sterile, i.e., microorganism free blood sample ranging in volume from 3 to 5 milliliters may raise the carbon dioxide level from 5 to 20 growth value units. An increase in one growth value units represents an increase of approximately 0.145 percent carbon dioxide (absolute) in the head space of the vial. Although, some sterile clinical blood samples have been observed to raise carbon dioxide background levels as much as 50 growth value units. The maximum increase in carbon dioxide concentration caused by blood metabolism usually occurs following a 24 hour to 5 day period of incubation. The increase is dependant on the type of growth medium utilized and the peculiarities of the blood sample being tested. The increases in carbon dioxide concentration due to metabolism of living blood cells introduce error in the detection of microorganisms present in the blood sample. In extreme cases the level of carbon dioxide caused by blood cell metabolism will cause the instrument to indicate a positive microorganism growth even in the absence of microorganisms in the sample.

Saponin, a non-ionic detergent plant extract was shown to be capable of reducing blood backgrounds while remaining non-toxic to most microorganisms. Also see, U.S. Pat. No. 3,858,045 to Waters. Saponin acts as a lysing agent which destroys erythrocytes and other mammalian cells present in blood cultures. At present, saponin must be added aseptically when used in blood culture vials, such as the Bactec ® non-radiometric culture vials NR-6, NR-7 and NR-8, as well as the radiometric Bactec ® culture vials described supra., due to the destruction of saponin's lytic capabilities when autoclaved in medium. As described in Example 1 and graphically illustrated FIG. 1, attempts to autoclave saponin present in culture medium at dilute concentrations, i.e. less than 2 mg/ml revealed that after autoclaving, saponin loses approximately ½ of its lytic capabilities.

In addition, since recent studies have reported that saponin binds preferentially to cholesterol, see Gogelein et al., supra, blood from different donors was tested in Example 4 having relatively high, and low serum total cholesterol levels. Upon visual inspection, the blood with higher cholesterol levels appeared not to have been lysed by the saponin as completely as the samples which had lower cholesterol levels. The samples containing the higher cholesterol levels also provided high carbon dioxide background readings when tested on the Bactec ® NR-660 instrument.

The present invention activates saponin in culture medium to transport, protect, modify or amplify saponin's lytic activity when it is subjected to autoclaving. The present invention also maintains the lytic activity of saponin in media when testing blood having a wide range of serum total cholesterol levels. In accordance with the present invention mixed-micelles of saponin and phospholipids are added to blood culture vials, such as the Bactec ® NR-6, NR-7, NR-8 culture vials. Useful concentrations of saponin may range from 2 mg/30 ml culture medium/vial, up to 1 g/30 ml culture medium/vial, depending on the donor's blood serum total cholesterol level. At concentrations below 4 mg per 30 ml culture medium/vial lysis often decline sharply, and at concentrations greater than 6 mg per 30 ml culture medium/vial highly b-nicotinamide adenine dinucleotide ("NAD") dependent strains of *Haemophilus influenza* are inhibited. Thus a preferred concentration of saponin ranges from about 4 mg/30 ml culture medium/vial to approximately 500 mg/30 ml culture medium/vial, most preferably from about 4 mg/30 ml culture medium/vial to 80 mg/30 ml culture medium/vial.

Saponin may be replaced by other detergents such as those suggested useful as hemolytic compounds by Zierdt, in "Simplified lysed-Blood Culture Technique", *Journal of Clinical Microbiology*, 23, 452-455, (1986) these includes sodium cholate, Tween 20, some of the Triton X series, Brijs 56, 58, 76, 78, 96 and 99, lysolecithin, polyoxyethylene-10-tridecyl ether, and other detergents that have been used to solubilize membranes. These detergents may show varying degrees of toxicity to different microorganism.

Saponin is activated and/or protected by use of an approximately equal or slightly greater amounts of phospholipid to prepare a suspension of mixed-micelles. The preferred phospholipid is L-α-lecithin, also referred to as phosphatidylcholine ("PC"). Other useful phospholipids are phosphatidylethanolamine ("PE"), sphingomyelin ("SM"), phosphatidylserine ("PS"), phosphatidylinositol ("PI"), phosphatidic acid ("PA"), and phosphatidylglycerol ("PG"). The following experiments indicated that the phospholipid concentrations should be equal to or slightly greater than the detergent concentration per vial for effective lysis. The preferred concentrations are from about 4 mg to about 20 mg phospholipid, most preferably about 8 mg PC, with 6 mg of saponin per thirty (30) ml medium in a Bactec ® culture vial. When the concentration of phospholipid is less than the detergent, the structure of the mixed-micelles and the properties of the detergent-lipid complex may change greatly, possibly reducing the synergy of the combination.

In accordance with the preferred procedure for preparing the PC/saponin mixed micelles of the present invention, phosophatidylcholine stored in a chloroform stock solution is dried under nitrogen, and lyophilized for at least 4 hrs. The lipids are re-suspended in concentrated saponin solution (about 12 mg PC per ml saponin in 10 mM phosphate buffered saline, pH 7.2) by alternatively vortexing vigorously and heating under hot running tap water. The cloudy to white suspension is then sonicated with a probe sonicator 5 min. off every 15 min. The suspension becomes clear in less than 1 hr. suggesting the formation of small, unilamellar mixed-micelles of PC/saponin. The PC/saponin micelles can be stored in phosphate buffered saline (pH 7.2) or in deionized water until needed, and then added in a desired concentration to the Bactec ® culture media.

The following examples further illustrates the various features of the present invention.

EXAMPLE 1

In order to determine the effect of autoclaving on the lytic activity of media containing dilute concentrations of saponin, i.e. less than 2 mg/ml, blood background $CO_2$ readings were determined on a Bactec ® NR-660 instrument using media containing saponin which had been aseptically added and compared to samples in which the saponin was autoclaved in the media.

A modified Bactec ® NR6A medium similar to commercial Bactec ® NR6A medium was prepared (500 ml) with triple the concentration of dextrose (1.8 g/L), niacinamide (0.01%) and pyruvate (0.1%) (Hereinafter referred to as the "modified Bactec ® NR6A medium"). The commercially available Bactec ® NR6A culture vials are known to contain the nutrients listed in Table 1. To a portion of the modified Bactec ® NR6A medium (150 ml), saponin was added at a concentration of 0.17 mg/ml(5 mg/30 ml medium). Both the modified Bactec ® NR6A medium and the modified Bactec ® NR6A medium with saponin were then bottled and autoclaved for fifteen minutes at 121° C.

A concentrated stock solution of saponin, Sigma (1988) Catalogue #S-1252, obtained from the Sigma Chemical Company, St. Louis, Mo. 63178 was prepared at a concentration of 50 mg/ml, and autoclaved for sterility. A one tenth milliliter (0.1 ml) aliquot of this stock solution was introduced thorough the septum using a hypodermic syringe with appropriate aseptic technique into two of the modified Bactec ® NR6A medium containing vials described above.

TABLE 1

BACTEC ® NR6A MEDIUM

| List of Ingredients | Amount |
|---|---|
| Deionized water | 30 ml |
| Soybean casein digest broth | 2.75% |
| Hemin | 0.0005% w/v |
| Vitamin K | 0.00005% w/v |
| Dextrose | 0.06% w/v |
| Sucrose | 0.0835% w/v |
| Sodium Polyanetholesulfonate (SPS) | 0.035% w/v |
| Antifoaming agent | 0.01 w/v |
| Pyridoxal HCl (Vitamin B6) | 0.001% w/v |

The Bactec ® NR6A media vials are dispensed with added $CO_2$.

Blood was obtained from a healthy donor and added in 5 ml aliquots to each of the following: two (2) vials containing modified Bactec ® NR6A medium (controls), two (2) vials containing modified Bactec ® NR6A with 5 mg saponin autoclaved in the media, and two (2) vials containing modified Bactec ® NR6A media with 5 mg saponin added aseptically. The vials were shaken at 260 rpm in a rotary shaker, placed in a 35° C. incubator and tested daily (twice in the first day) for increases in head space carbon dioxide on a Bactec ® 660 instrument. The average growth value of each pair of vials is plotted in FIG. 1.

Figure 1:
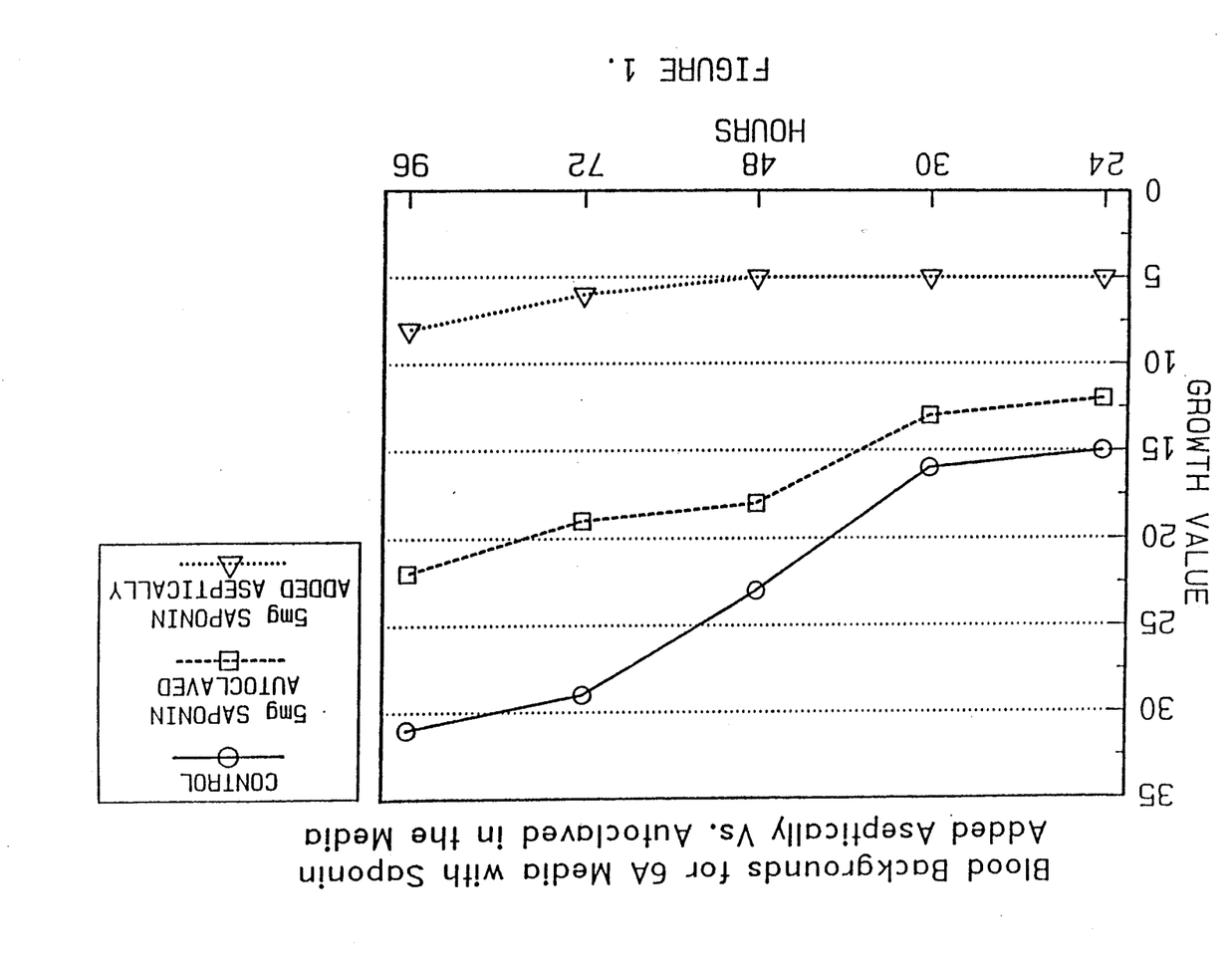
FIG. 1 is a graph illustrating the growth value versus time for blood cultures with saponin added aseptically ("△"), saponin autoclaved in the medium ("□") and a saponin free control medium ("O") as described in Example 1.

As shown in FIG. 1, autoclaving a dilute solution of saponin in media resulted in saponin losing approximately one-half of its hemolytic activity, as compared with aseptically added saponin, as demonstrated by metabolic production of $CO_2$. By contrast, the control vials which did not contain saponin showed much higher rates of metabolic activity.

EXAMPLE 2

In order to test the effects of increased levels of cholesterol in the blood of a donor on the hemolytic activity of saponin, the blood of a donor was spiked with various levels of cholesterol utilizing phosphatidylcholine ("PC")/cholesterol complexes prepared in accordance with the method of Bittmann, *Biochemistry*, 11, 4831–4839, (1972); and Schullery, *Biochemistry*, 19, 3919–3923 (1980) utilizing egg phosphatidylcholine described as L-α-lecithin >95% pure in Avanti catalogue No. 131601, purchased from Avanti Polar Lipids, Pelham, Ala. 35124 ("Avanti"). The method was used in an effort to circumvent the insolubility of cholesterol in an aqueous environment and to mimic the forms in which cholesterol naturally occurs in blood. The PC/cholesterol "complexes" were, theoretically, PC/cholesterol vesicles. Since the exact nature of these structures has not been experimentally determined, they shall be referred to as PC/cholesterol complexes.

First, two 0.02 ml samples of serum were tested from each of three donors for serum total cholesterol levels utilizing the recommended procedure of a commercially available assay kit, Stanbio Enzymatic Cholesterol Procedure No. 1010, Stanbio Laboratories, San Antonio, Tex. 78202. It was found that the serum total cholesterol level of the blood from Donor I was 164 mg/dL, from donor II was 179 mg/dL, and from Donor III was 239 mg/dL.

Ten (10) vials of commercially produced Bactec ® NR6A medium were prepared as follows: To five (5) of the vials was added 0.1 ml saponin from the 50 mg/ml sterile saponin stock solution prepared in Example 1 (these vials are referred to as the saponin set, as opposed to the other five vials which are referred to as the control set). To one (1) vial from each set 8.2 mg sonicated PC vesicles were added. To another three (3) vials from each set 0.5 ml, 1.0 ml and 1.5 ml, respectively, of a solution of PC/cholesterol complexes were added to increase the level of serum total cholesterol of the blood from Donor I in these vials by concentrations of 25 mg/dL, 50 mg/dL and 75 mg/dL, respectively. Five (5)ml of fresh blood from Donor I was added aseptically to each vial in both the saponin set and the control set. All vials were then shaken and tested on the Bactec ® NR-660 instrument according to the procedure described in Example 1.

Figure 2:
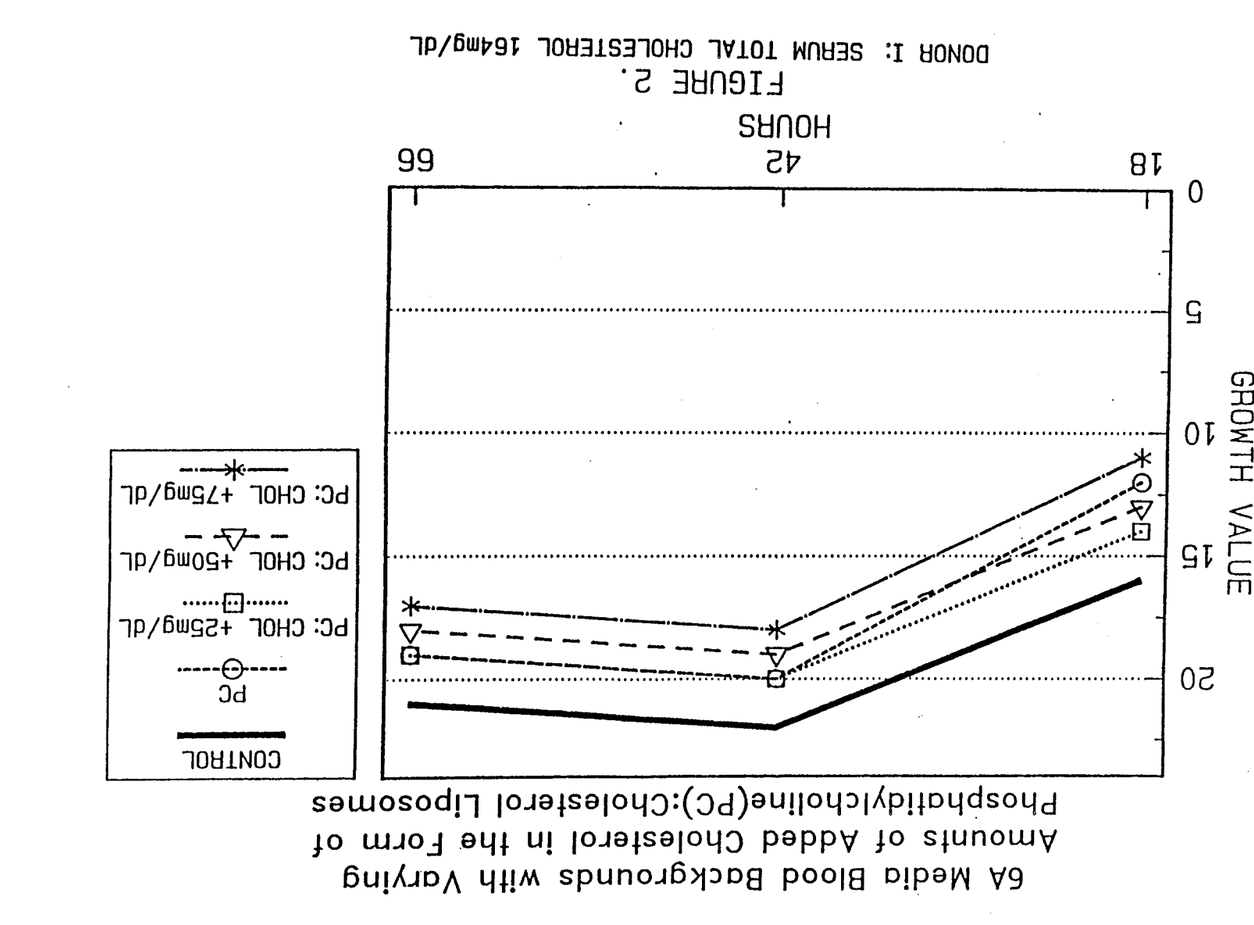
FIG. 2 is a graph illustrating the effect of increased serum cholesterol levels on blood background $CO_2$ readings in the presence of phosphatidylcholine liposomes. The control, shown as the dark line contains medium plus blood having a serum total cholesterol level of 164 mg/dL; another control having PC liposomes added ("O") also includes the blood sample having a serum total cholesterol level of 164 mg/dL; three (3) additional sets of samples include PC:cholesterol complexes added to the blood sample to increase the blood serum total cholesterol level by 25 mg/dL ("□"), 50 mg/dL ("△") and 75 mg/dL ("*") respectively, as described in Example 2.
Figure 3:
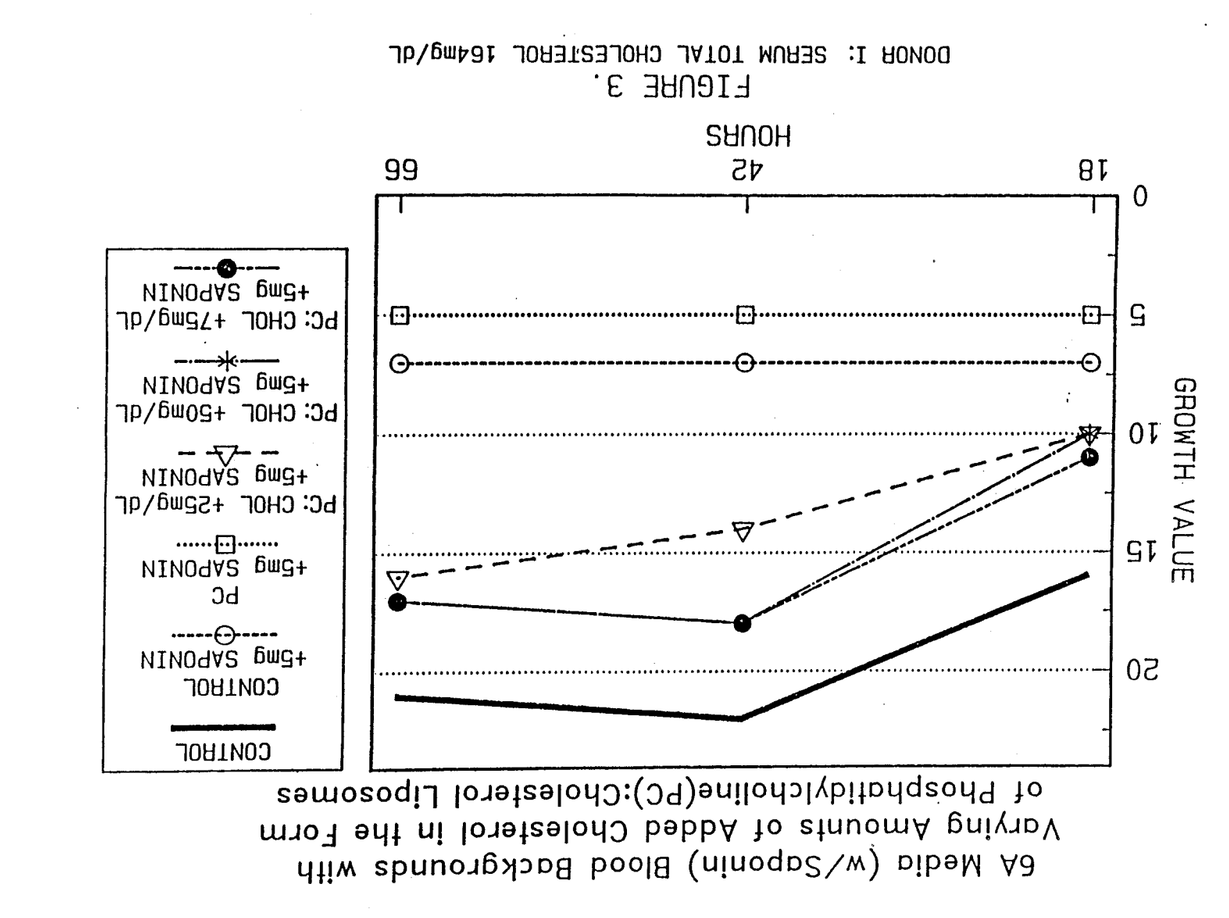
FIG. 3 is a graph illustrating the blood $CO_2$ background readings of the same samples shown in FIG. 2, except for the presence of 5 mg saponin added to each medium sample. The saponin free control shown as the dark line in FIG. 2 was transposed onto this graph for comparison.

FIGS. 2 and 3 show the growth values, i.e. blood $CO_2$ background readings of these samples over a 64 hour period. The growth values for the PC and saponin free control (shown in the dark line in FIG. 2) are transposed onto FIG. 3 for comparison.

Visual inspection of the saponin containing samples showed decrease of blood lysis as cholesterol levels increased. Lysis is evidenced by the color change of blood/media from bright red to a very dark shade of red. As graphically illustrated in FIGS. 2 and 3 all samples showed some reduction of growth value with the addition of saponin. Surprisingly, the control sample which contained both PC and saponin ("□" of FIG. 3) showed lower growth values than the same sample with saponin alone ("O" of FIG. 3) even at a relatively low to normal blood serum total cholesterol level of 164 mg/dL. At the higher cholesterol levels of 189 mg/dL (25 mg/dL added), 214 mg/dL (50 mg/dL added) and 239 mg/dL (75 mg/dL added), respectively, some reduction of growth values were observed in the presence of the combination of PC and saponin.

Accordingly, the following experiments were performed to determine whether a particular combination of PC and saponin could be effectively used to reduce blood background growth values over a broad range of blood serum cholesterol levels.

EXAMPLE 3

The experiments described in Example 2 utilized egg PC, however, a much less expensive form of phosphatidylcholine is extracted from soybeans and is available from Avanti Polar Lipids as a soybean phosphatide extract in paste form, Avanti Catalogue #441601. The soybean phosphatide extract is a much more crude preparation than the egg PC, and is not recommended by the manufacturer as being suitable for the preparation of stable liposomes due to its contamination primarily by lysolecithin. It was found in this example, however, that a suspension of soy PC could be sonicated sufficiently, from its opaque, white appearance to a clearer, slightly cloudy suspension indicating a smaller particle size. Since saponin is a detergent which solubilizes liposomes or membranes, we hypothesized that the saponin and the PC were forming mixed-micelles of detergent and lipid when the PC was introduced into the media described in Example 2. Since the long term stability of the PC liposomes was not a crucial factor in these preliminary experiments, the less expensive soybean PC was substituted for egg PC.

To test the background $CO_2$ reducing capabilities of media containing both soy PC and saponin, two different methods of preparation were utilized. In the first method, soy PC liposomes were prepared and then added to a Bactec ® NR6A culture medium containing saponin. In the second method, a sonicated suspension or solution containing both PC and saponin was prepared and then added to Bactec ® NR6A medium (since it is not clear whether the mixed-micelles are in a true solution or suspension the term "suspension" is being used to designate either condition).

In performing the first method, soy PC liposomes were prepared according the method of Schullery et al. in, *Biochemistry*, 19, 3919–3923 (1980). The soy PC was stored in a paste form. Two hundred (200)mg of soy PC paste was weighed in a glass vial, and enough chloroform was added to dissolve the paste (<5 ml). Once the lipids were fully dissolved, the chloroform was dried under a stream of nitrogen, leaving a thin film of lipid around the inside of the vial. Since it was important to remove all of the chloroform for the lipids to successfully sonicate into small liposomes, the chloroform was removed overnight under a vacuum of 5 microns Hg (condenser temperature −70° C.). The lyophilizer used for these experiments was the Labconco #7510, manufactured by Labconco Corporation, Kansas City, Mo. 64132, attached to a Maxima D8A vacuum pump manufactured by Fisher Scientific, Pittsburgh, Pa. 15219. The lipids were then resuspended in 10 mM potassium phosphate buffer pH 7.2, by alternately vortexing vigorously and heating the vial under hot running tap water. The suspension appeared a milky white, indicating the formation of large, multilamellar vesicles. The suspension was then sonicated with a probe sonicator, model w-225r manufactured by Heat Systems-Ultrasonics Inc., Plainview, N.Y. 11803, for approximately one hour with 5 minutes off for every 15 minutes on. The suspension became clearer, suggesting that the large multilamellar vesicles had broken down to small unilammellar vesicles.

To perform the second method, the first method, as described above, was modified so that 100 mg of lyophilized PC was resuspended with a saponin solution having a concentration of 12 mg/ml saponin in 10 mM potassium phosphate buffer pH 7.2, vortexed and sonicated as described above. The PC/saponin suspension sonicated to clear in approximately 30 minutes, about one-half the time it took to sonicate PC alone. This indicated that smaller, more stable PC/saponin mixed-micelle complexes were formed.

One-half (0.5)ml aliquots of the suspension prepared by the first method were then pipetted into 12 vials. To six (6) of these vials the modified Bactec ® NR6A medium was added at a volume of 30 ml medium/vial, and to the other six vials the same medium preparation which also contained saponin at a concentration of 0.2 mg/ml (6 mg saponin/vial) was added to each vial in a volume of 30 ml medium/vial. Next, one-half (0.5)ml aliquots of the suspension prepared by the second method were pipetted into six (6) vials. To each of these six (6) vials 30 ml of the modified Bactec ® NR6A medium was added. Six (6) control vials were prepared, each containing 30 ml of the modified Bactec ® NR6A medium. Six (6) additional vials were prepared, each containing 30 ml each of the modified Bactec ® NR6A medium with saponin at a concentration of 0.2 mg/ml. In total, five types of media were prepared: (1) modified Bactec ® NR6A, (2) modified Bactec ® NR6A with saponin, (3) modified Bactec ® NR6A with soy PC, (4) modified Bactec ® NR6A with soy PC and saponin added separately, and (5) modified Bactec ® with soy PC and saponin added as a sonicated suspension. All media were capped and autoclaved at 121° C. for 17 minutes.

The vials containing PC and saponin were then visually compared for clarity. The medium prepared according to the second method was noticeably clearer than the medium prepared according to the first method. Five (5)ml of blood from Donors II (low cholesterol) and III (high cholesterol) which were tested for serum total cholesterol levels in Example 2, were added to one (1) vial of each of the five (5) types of media prepared above (one set of five (5) vials per donor). All vials were then shaken and tested on the Bactec ® NR 660 instrument according to the procedure described in Example 1. The growth values determined in these tests are plotted on FIGS. 4 (Donor II) and 5 (Donor III).

Figure 4:
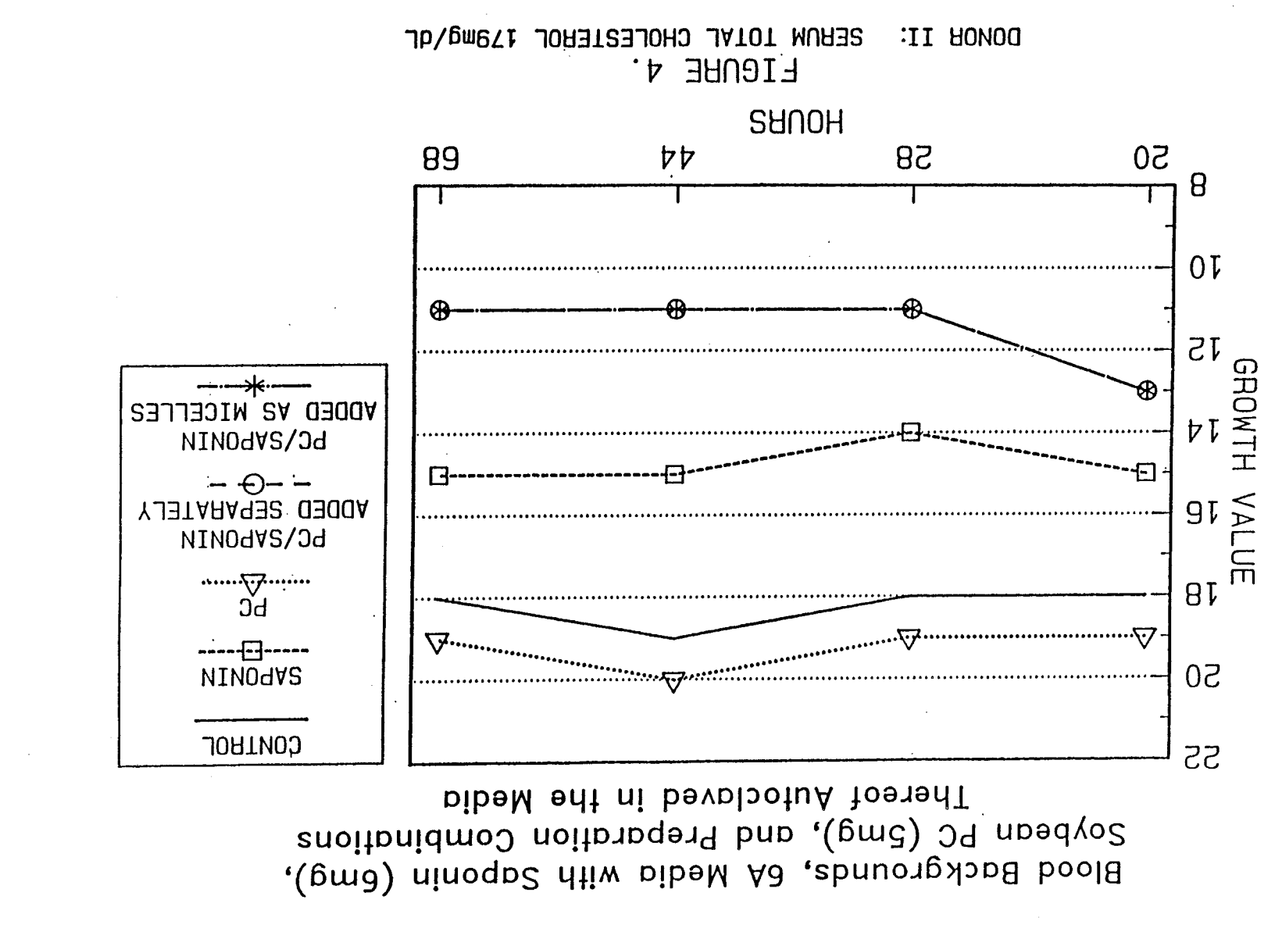
Figure 5:
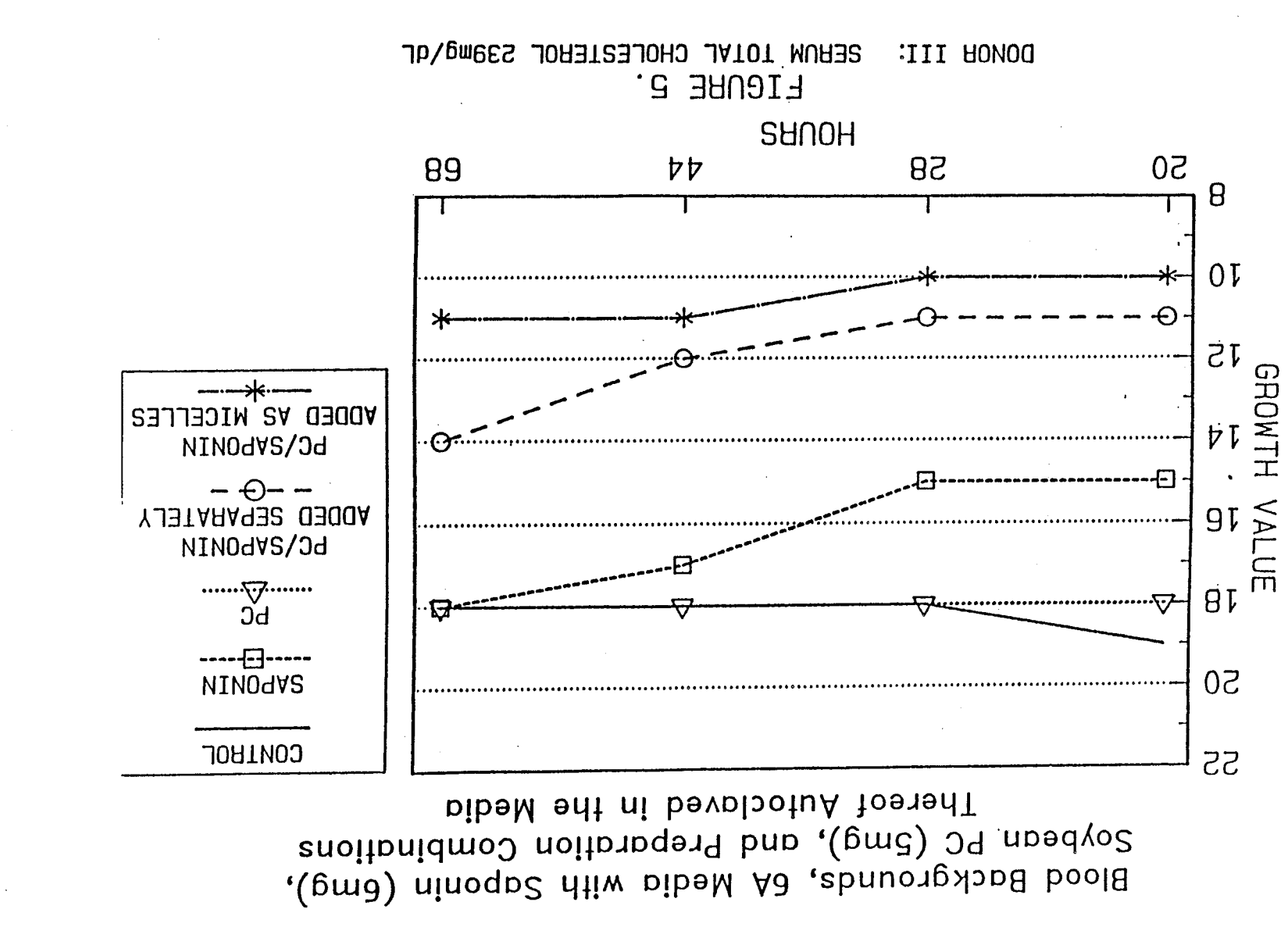
FIG. 5 is a graph illustrating the reduction of $CO_2$ background readings of blood from a high cholesterol donor (Donor III-239 mg/dL) after adding PC and saponin to modified Bactec ® NR6A medium either separately (first method), or as a sonicated mixed-micelle solution (second method), as described in Example 3. Except for using blood from Donor III, all samples and designations are the same as described for FIG. 4, above.

The vials containing both PC and saponin consistently showed lower background $CO_2$ levels in both the samples having a low serum total cholesterol level (Donor II-179 mg/dL) shown in FIG. 4, and a high serum total cholesterol level (Donor III-239 mg/dL) shown in FIG. 5. Furthermore, the vials containing PC and saponin sonicated together, which were prepared in accordance with the second method, showed a reduction in growth values which was either equivalent (for the low cholesterol Donor II) or lower (for the high cholesterol Donor III) than the vials containing PC and saponin added separately, which were prepared in accordance with the first method. Due to these advantages, and additionally, since the sonicated PC/saponin prepared according to this method took less time to prepare, the second method for preparing the PC/saponin containing medium was selected as the preferred method of this invention and was utilized in the following Examples.

EXAMPLE 4

Blood samples which lie at relatively higher and relatively lower extremes of serum total cholesterol levels than those tested in Example 3, were tested in medium containing saponin, and in medium containing sonicated mixed-micelles of PC/saponin. The purpose of this experiment was to determine the relative effect of extreme blood serum cholesterol levels on the hemolytic activity of medium containing sonicated PC/saponin mixed-micelles as compared to the hemolytic activity of medium containing saponin alone.

Samples of fresh blood drawn from Donor IV and V were tested for serum total cholesterol in accordance with the method described in Example 2. The serum total cholesterol level of the blood from Donor IV was determined to be "high" measuring 270 mg/dL. The serum total cholesterol level of Donor V was determined to be "low", measuring 150 mg/dL.

Three liters of modified Bactec ® NR6A medium was prepared as described in Example 1, and separated into three (3)-one (1) liter aliquots. The first liter was used as the control medium. The second liter of medium was combined with 200 mg saponin to yield a final concentration of 0.2 mg saponin/ml of medium (6 mg saponin/30 ml medium/vial). The third liter of medium was combined with a concentrated suspension of soy PC/saponin mixed-micelles prepared according to the second method described in Example 3, to yield a final concentration of 0.33 mg PC/0.20 mg saponin per ml medium (10 mg PC/6 mg saponin per 30 ml medium/vial). Each of the media was separated into 30 ml aliquots in Bactec ® media vials and autoclaved at 121° C. for seventeen minutes. Four (4) vials from each type of medium prepared for this experiment were reserved for testing organism growth (See, Example 5).

Twelve (12), 5 ml blood samples, six (6) from Donor IV and six (6) from Donor V, were aseptically introduced into separate Bactec ® culture vials containing 30 ml of one of the media described above. Thus, for each Donor's blood samples, one pair of vials contained modified Bactec ® NR6A medium, a second pair of vials contained saponin containing modified Bactec ® NR6A medium, and a third pair of vials contained the PC/saponin mixed-micelles containing modified Bactec ® NR6A medium. Upon visual inspection, the high cholesterol samples from Donor IV appeared to not have lysed as completely in the saponin containing vials as the samples determined to have lower cholesterol levels supplied by Donor V.

Figure 6:
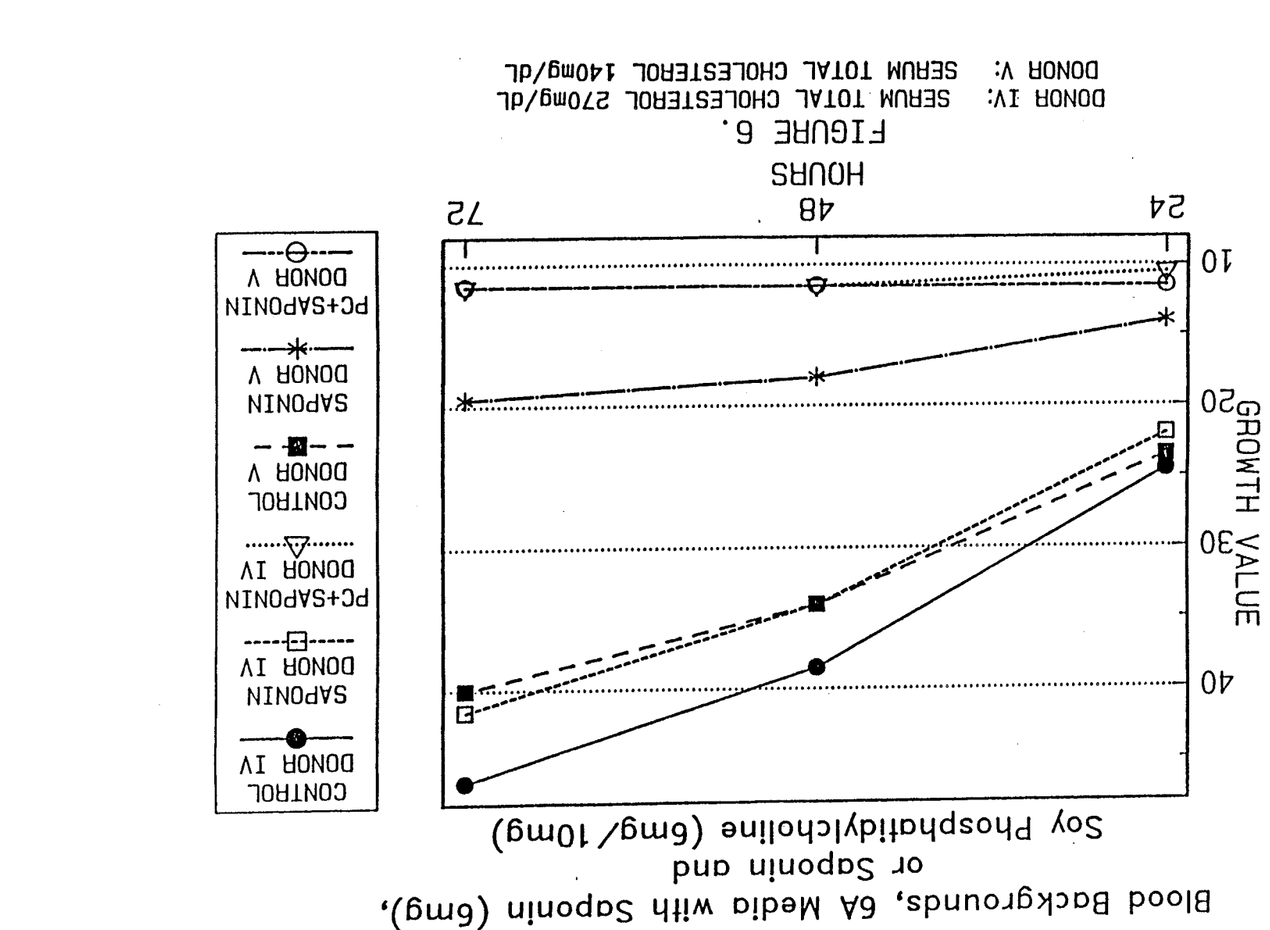

The samples were then tested for carbon dioxide background readings on a Bactec ® NR-660 instrument in accordance to the procedure described in Example 1. The results of these tests were plotted as FIG. 6. As shown on FIG. 6, the high cholesterol samples supplied by Donor IV tested higher for carbon dioxide background readings than the low cholesterol samples supplied by Donor V. In addition, the soy PC/saponin mixed-micelles containing medium reduced the background levels of $CO_2$ equally for blood samples from both donors. In contrast, the medium containing saponin alone, while causing a significant reduction in the background $CO_2$ readings of blood from the low cholesterol donor, only caused a very minor reduction in the background $CO_2$ readings of blood from the high cholesterol donor.

EXAMPLE 5

The modified medium prepared in Example 4 and reserved for this Example, was used for testing the growth of Haemophilus influenza (H. influenza). As described in Example 1, the modified Bactec ® NR6A medium contained niacinamide. Niacinamide was included in the media preparation to inhibit NADase, an enzyme released from blood cells when they are lysed. NADase depletes the amount of b-nicotinamide adenine dinucleotide (NAD) available to organisms. NAD is found in blood, and is required for the growth of some organisms such as H. influenza. Thus, NAD dependent strains such as H. influenza would not grow well, if at all, in medium with lysed blood, unless the NADase inhibitor, niacinamide, is also present to inhibit the released NADase and stop the depletion of NAD available to the organisms. Accordingly, this Example shows that the preferred medium of the present invention is useful for detection of growth even for very fastidious organisms.

Eighteen (18) strains of H. influenza were taken from frozen stock cultures originally isolated from clinical specimens and tested for growth in lysed blood cultures, i.e. known to contain large amounts of NADase, with and without niacinamide. The two most NAD dependent strains, as determined by this test (strains 337 and 340), were selected for the following experiment.

In three (3) pairs of vials, each pair containing one of the three (3) types of modified media reserved from Example 4, 5 ml samples of blood from Donors IV and V, respectively (i.e., one set of three (3) vials for each donor), were aseptically added. Each vial containing the blood of Donor IV was then inoculated with 0.1 ml of a $1 \times 10^4$ cfu/ml inoculum of H. influenza strain 337. Similarly, each vial containing the blood of Donor V was innoculated with 0.1 ml of a $1 \times 10^4$ cfu/ml inoculum of H. influenza strain 340. The samples were then tested for background carbon dioxide readings on a Bactec ® NR-660 instrument in accordance with the procedure described in Example 1. The times to detection of growth of these organisms (TTD), and the average growth value (GV) for each type of media are shown in Table 2.

TABLE 2

| Donor/ | MEDIA | | | | | |
|---|---|---|---|---|---|---|
| | Control | | Saponin | | PC + Saponin | |
| H. Influenza Strain | TTD | GV | TTD | GV | TTD | GV |
| IV/337 | 24 | 105 | 24 | 122 | 24 | 110 |
| V/340 | 24 | 109 | 24 | 117 | 48 | 134 |

TTD - TIME TO DETECTION (HRS.) GV - GROWTH VALUE

Table 2 shows that growth of even the most NAD dependent strains of H. Influenza can still be detected in the PC/saponin modified medium of this invention, despite the improved lytic action of PC/saponin containing medium over both the control medium and the medium containing saponin alone. The lag in detection time for the Donor V/340 strain in PC/saponin medium is probably due to the combined effect of the low cholesterol levels in the blood of Donor V and the improved efficiency of blood lysis by this medium, therefore more rapidly and effectively releasing NADase from the blood cells into the medium.

EXAMPLE 6

The advantages of the phospholipid/saponin micelles in the preferred medium of the present invention are believed to be due to the action of the phospholipid either somehow protecting the saponin during autoclaving or increasing saponin's lytic properties by transporting the saponin or amplifying its actions. The following experiment tests the hypothesis that the phospholipid protects saponin during autoclaving.

First, PC/saponin micelles are prepared in accordance with the second method described in Example 3. Half of this mixture is added to modified Bactec® NR6A medium prepared in accordance with the procedure described in Example 1. The medium is then bottled and autoclaved at 121° C. for 15 minutes. The remaining concentrated PC/saponin suspension is also autoclaved at 121° C. for 15 minutes. Aliquots of the autoclaved suspension of PC/saponin mixed-micelles are then aseptically introduced through the septa of a number of bottles of modified Bactec® NR6A medium which have been autoclaved. Additional media samples prepared for this example also include: (1) modified Bactec® NR6A medium prepared as described in Example 1, (2) ) modified Bactec® NR6A medium with 6 mg saponin per vial added aseptically, as described in Example 1, (3) modified Bactec® NR6A medium with 6 mg saponin per vial, autoclaved in the medium as described in Example 1.

Five (5)ml aliquots of blood from healthy donors, one having a normal serum total cholesterol level and the other having a high serum total cholesterol level, are separately added to each of the vials containing the various media described above. The vials are incubated and tested for carbon dioxide producing metabolism according to the procedure described in Example 1. Blood background $CO_2$ levels of media types 1 through 3 are expected to be similar to those backgrounds plotted on FIG. 1 for the normal cholesterol samples, and higher growth values are expected for the high cholesterol samples to which saponin was added, conforming to the results shown in FIGS. 3 and 4. The background readings for both sets of media samples containing PC/saponin mixed-micelles are expected to approximate a straight line with a slope very close to zero and a y-intercept of about five (5). This example shows that whatever causes medium containing dilute concentration of saponin to lose its lytic activity after autoclaving, does not cause a similar loss of lytic activity after autoclaving in medium containing mixed-micelles of phospholipid/saponin at similar saponin concentrations.

EXAMPLE 7

The PC/saponin mixed-micelles prepared in accordance with the second method of Example 3, at a concentration of 10 mg PC and 6 mg saponin, were tested and sized in accordance with their light scattering capability using a Coulter model N4S particle sizing instrument, Coulter Electronics, Inc., Hialeah, Fla. 33010. The PC/saponin mixed-micelles were suspended in each of the following carriers: (1) 30 ml deionized water, (2) 30 ml potassium phosphate buffered saline (PBS) pH 7.2, and (3) 30 ml Bactec® NR6A medium. The results of the light scattering tests for the PC/saponin mixed-micelle suspensions are shown in Table 3.

TABLE 3

| Sample | Mean diameter of particle (nm) |
| --- | --- |
| 10 mg PC, 6 mg saponin in 30 ml deionized water | 65 |
| 10 mg PC, 6 mg saponin in 30 ml PBS | 77 |
| 10 mg PC, 6 mg saponin in 30 ml Bactec® NR6A medium | ~200 |

Analysis on the Coulter instrument indicated that there were at least two particle size populations in the Bactec® NR6A medium. The first, having particles approximately 200 nm in diameter, and the second having particles approximately 2100 nm in diameter. The mean diameter of the particles in the Bactec® NR6A medium changed over time suggesting aggregation of the particles. It was observed that over a period of a day or more, the particles appeared to settle out of the medium. The aggregation and settling of particles was not observed in deionized water or PBS. The settling that occured in the medium is probably a result of the many peptides that are found in the medium that aggregated with the micelles.

EXAMPLE 8

Other phospholipids were tested to determine whether they could be substituted for phosphatidylcholine (PC) to form the mixed micelles of the present invention. The lipids chosen for this experiment were phosphatidylethanolamine (PE), Avanti Catalogue No. 841118, and sphingomyelin (SM), Avanti Catalogue No. 860061. Both of these phospholipids were chosen because of their similar structures to that of PC, and because all three of these lipids are found in erythrocyte membranes.

Mixed micelles of each of the SM and PE phospholipids were prepared with saponin in accordance with the second method described in Example 3 for PC/saponin. The sonicated phospholipid/saponin solutions were then each added to 300 ml of the modified Bactec® NR6A medium as described in Example 1, stirred, and dispensed into ten culture vials in a quantity of 30 ml/vial. The concentration of phospholipid to saponin per vial was 10 mg to 6 mg, respectively. Four types of media were prepared for testing: (1) modified Bactec® NR6A medium (control), (2) modified Bactec® NR6A medium with 6 mg saponin per vial as described in Example 4, (3) modified Bactec® NR6A medium with SM/saponin mixed micelles as described above, and (4) modified Bactec® NR6A medium with PE/saponin mixed micelles as described above. All media were then capped and autoclaved at 121° C. for 17 minutes.

Figure 7:
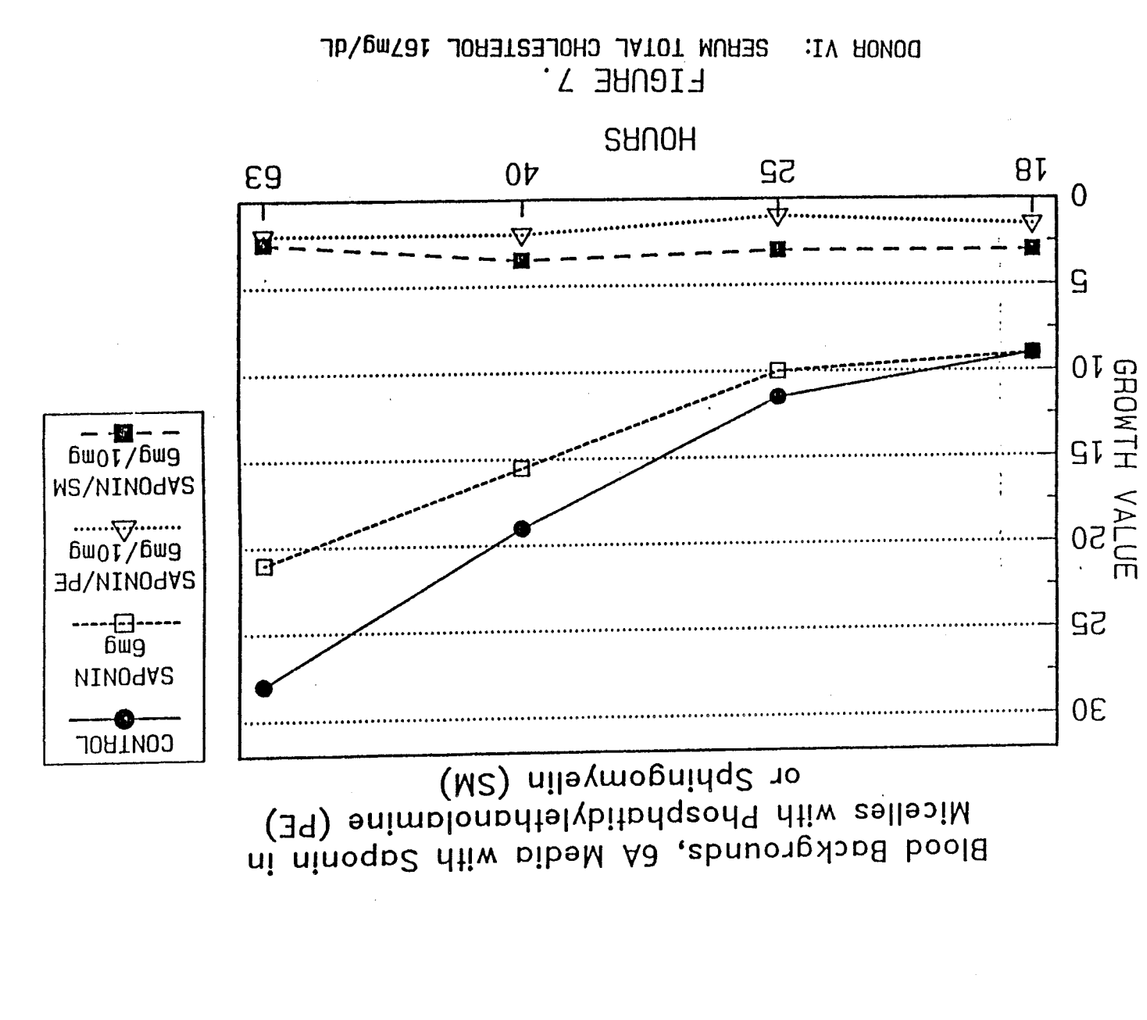
FIG. 7 is a graph illustrating the background $CO_2$ readings of media samples, each containing blood having a low serum total cholesterol level, 167 mg/dL. The samples tested included a modified Bactec ® NR6A control medium ("●"), modified medium further containing 6 mg saponin ("□"), modified medium further containing mixed-micelles of saponin/PE in a ratio of 6 mg saponin to 10 mg PE per vial ("△"), and modified medium further containing mixed micelles of saponin/SM in a ratio of 6 mg saponin to 10 mg SM per vial ("■"), as described in Example 8.
Figure 8:
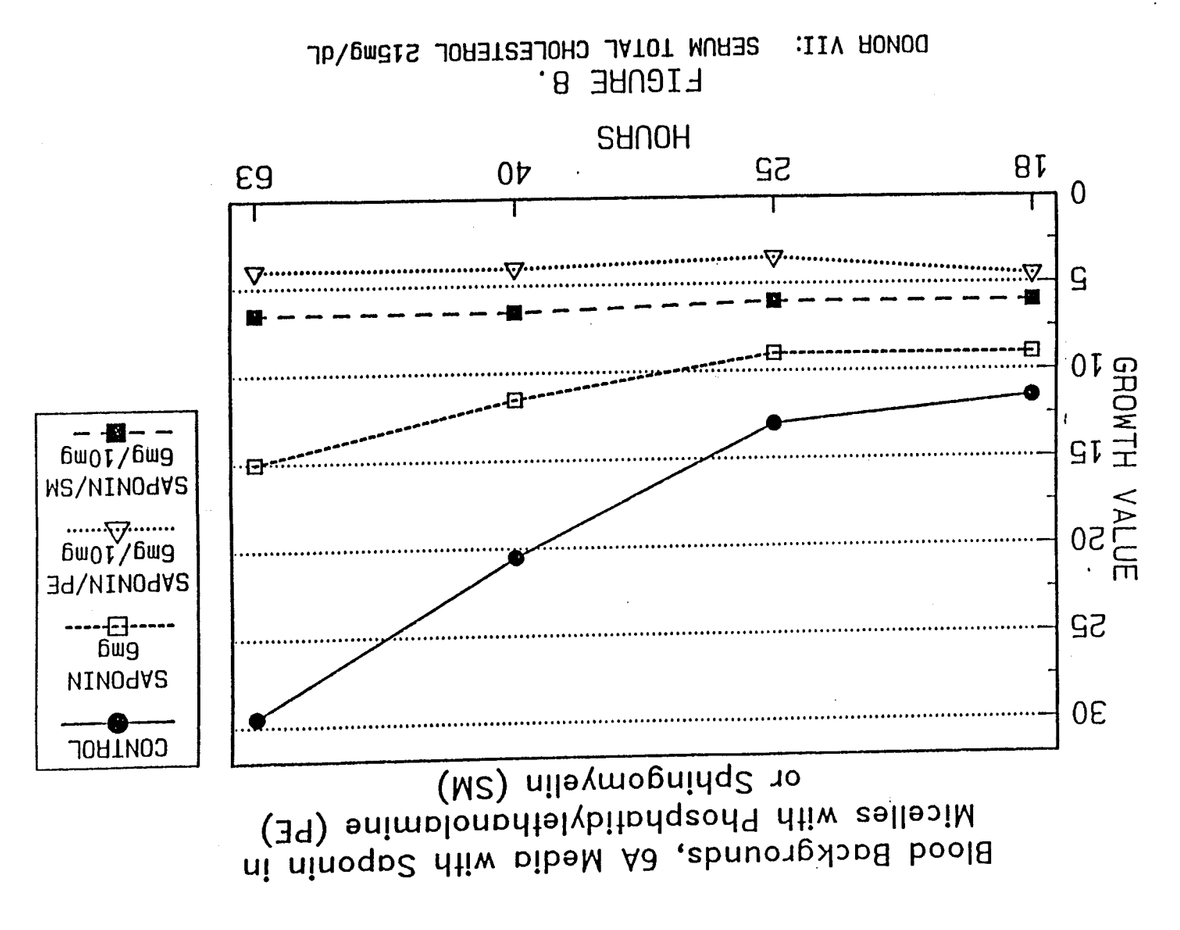
FIG. 8 is a graph illustrating the background $CO_2$ readings of media samples, each containing blood having a high serum total cholesterol level, 215 mg/dL. The samples tested included a modified Bactec ® NR6A control medium ("●"), modified medium further containing 6 mg saponin ("□"), modified medium further containing mixed micelles of saponin/PE in a ratio of 6 mg saponin to 10 mg per vial ("△"), and modified medium further containing mixed micelles of saponin/SM in a ratio of 6 mg saponin to 10 mg SM per vial ("■") as described in Example 8.

Each medium was tested in duplicate using 5 ml blood per vial from two different donors who were tested for serum total cholesterol in accordance with the method described in Example 2. Donor VI had a serum total cholesterol level of 167 mg/dL while Donor VII had a serum total cholesterol level of 215 mg/dL. The growth and metabolism in these vials was tested in accordance with the procedure described in Example 1 and the growth values vs. time are plotted in FIG. 7 (for Donor VI) and FIG. 8 (for Donor VII). Both FIGS. 7 and 8 show a marked decrease in the blood background $CO_2$ levels of the SM/saponin and PE/saponin samples for both donors, as compared with the control and the saponin only samples. We note that in FIG. 8 the backgrounds for the lipid/saponin containing media are higher than the backgrounds for the same media in FIG. 7. This is probably due to the higher cholesterol level of Donor VII. What is most important, however, is that the backgrounds for both of these phospholipid/saponin containing media show no increase from day to day, even with elevated cholesterol levels.

These results suggest that other phospholipids, besides PE and SM could be used to form liposomes which transport, protect, modify or amplify saponin and its capability to lyse mammalian blood cells. Other phospholipids which may prove useful include: phosphatidylserine (PS), phosphatidylinositol (PI), phosphatidic acid (PA) and phosphatidylglycerol (PG).

Thus, while there have been described what are the presently contemplated preferred embodiments of the present invention, further changes and modifications could be made by those skilled in the art without departing from the spirit and scope of the invention, and it is contemplated to claim all such changes and modifications.

We claim:

1. A growth medium for detecting biological activity in blood which comprises a carbon source which can be metabolized by a microorganism to produce carbon dioxide, an effective amount of a lysing agent and a phospholipid, wherein said lysing agent and phospholipid are formed in mixed micelles.

2. A growth medium in accordance with claim 1, wherein said lysing agent is a detergent selected from the group consisting of saponin, sodium cholate, Tween 20, members of the Triton X series, Brijs 56, 58, 76, 78, 96, 99, lysolecithin and polyoxyethylene-10-tridecyl ether.

3. A growth medium in accordance with claim 1, wherein said phospholipid is selected from the group consisting of phosphatidylcholine, phosphatidylserine, phosphatidylinositol, phosphatidic acid, phosphatidylglycerol, phosphatidyethanolamine, and sphingomyelin.

4. A growth medium in accordance with claim 2 wherein said detergent lysing agent is saponin.

5. The growth medium in accordance with claim 4, wherein the concentration of saponin ranges from about 2 mg saponin/30 ml medium to about 1 g saponin/30 ml medium.

6. The growth medium in accordance with claim 4, wherein the concentration of saponin ranges from about 4 mg saponin/30 ml medium to about 60 mg saponin/30 ml medium.

7. The growth medium in accordance with claim 6, wherein the concentration of saponin ranges from about 4 mg saponin/30 ml medium to about 6 mg saponin/30 ml medium.

8. A growth medium in accordance with claim 2, wherein said detergent lysing agent is present in a concentration from about 0.02% to about 2%.

9. A growth medium in accordance with claim 8, wherein said detergent lysing agent is present in a concentration form about 0.05% to about 1%.

10. A growth medium in accordance with claim 2, wherein the concentration of said phospholipid is greater than or equal to the concentration of said detergent lysing agent.

11. An improved method for detecting biological activity in blood wherein a growth medium including a carbon source which can be metabolized by a microorganism to produce carbon dioxide is inoculated with a blood sample, the inoculated sample is incubated under conditions conducive to the occurrence of normal metabolic processes for a period of time sufficient to cause production of carbon dioxide by metabolism of a microorganism present in the blood sample and at least a portion of the gaseous atmosphere from the incubation is analyzed to determine the presence of carbon dioxide, the improvement comprising incorporating into the growth medium an effective amount of a detergent lysing agent and a phospholipid, wherein said lysing agent and phospholipid are formed in mixed micelles, and whereby the level of carbon dioxide produced by blood cell metabolism is reduced or eliminated over a broad range of blood cholesterol levels.

12. A method in accordance with claim 11, wherein said lysing agent is selected from the group consisting of saponin, sodium cholate, Tween 20, members of the Triton X series, Brijs 56, 58, 76, 78, 96, 99, lysolecithin and polyoxyethylene-10-tridecyl ether.

13. A method in accordance with claim 11, wherein said phospholipid is selected from the group consisting of phosphatidylcholine, phosphatidylserine, phosphatidylinositol, phosphatidic acid, phosphatidylglycerol, phosphatidyethanolamine, and sphingomyelin.

14. A method in accordance with claim 12 wherein said detergent lysing agent is saponin.

15. A method in accordance with claim 14, wherein the concentration of saponin ranges from about 2 mg saponin/30 ml medium to about 1 g saponin/30 ml medium.

16. A method in accordance with claim 15, wherein the concentration of saponin ranges from about 4 mg saponin/30 ml medium to about 500 mg saponin/30 ml medium.

17. A method in accordance with claim 16, wherein the concentration of saponin ranges from about 4 mg saponin/30 ml medium to about 80 mg saponin/30 ml medium.

18. A method in accordance with claim 17, wherein the concentration of saponin ranges from about 4 mg saponin/30 ml medium to about 8 mg saponin/30 ml medium, whereby said medium is useful for testing fastidious microorganisms.

19. A method in accordance with claim 11, wherein said detergent lysing agent is present in a concentration from about 0.02% to about 2%.

20. A method in accordance with claim 19, wherein said detergent lysing agent is present in a concentration form about 0.05% to about 1%.

21. A method in accordance with claim 11, wherein the concentration of said phospholipid is greater than or equal to the concentration of said detergent lysing agent.

22. A method in accordance with claim 3 wherein the phospholipid is phosphotidylcholine.

23. A method in accordance with claim 13 wherein the phospholipid is phosphotidylcholine.

* * * * *